United States Patent [19]

Nawracaj et al.

[11] 4,071,033
[45] Jan. 31, 1978

[54] ELECTROTHERAPEUTIC DEVICE WITH MODULATED DUAL SIGNALS

[76] Inventors: Edward P. Nawracaj, 8349 Walredon Ave., Burr Ridge, Ill. 60521; Henry A. Greit, 3527 W. 80th St., Chicago, Ill. 60652

[21] Appl. No.: 752,597

[22] Filed: Dec. 20, 1976

[51] Int. Cl.$^2$ .............................................. A61N 1/36
[52] U.S. Cl. .................................. 128/420 A; 128/422
[58] Field of Search ........... 128/419 R, 420 A, 420 R, 128/421, 422, 423

[56]  References Cited

U.S. PATENT DOCUMENTS

| | | | |
|---|---|---|---|
| 2,622,601 | 12/1952 | Nemec | 128/422 |
| 3,096,768 | 7/1963 | Griffith, Jr. | 128/420 A |
| 3,774,620 | 11/1973 | Hansjürgens | 128/420 A |
| 3,794,022 | 2/1974 | Nawracaj et al. | 128/420 A |
| 3,835,833 | 9/1974 | Limoge | 128/420 R X |
| 3,918,461 | 11/1975 | Cooper | 128/420 A |
| 3,958,577 | 5/1976 | Rodler | 128/420 A |

FOREIGN PATENT DOCUMENTS

| | | | |
|---|---|---|---|
| 2,159,437 | 4/1973 | Germany | 128/420 A |
| 888,580 | 1/1962 | United Kingdom | 128/419 R |

*Primary Examiner*—William E. Kamm
*Attorney, Agent, or Firm*—Kirkland & Ellis

[57]  ABSTRACT

Stimuli are initiated by a master oscillator, whose output is split and applied to two frequency dividers which divide the frequency by different numbers. The two frequencies thus derived are applied to waveshapers to provide a desired waveform such as a half sinewave, and also each signal is further divided by a common number. The two signals are then amplified, and applied to the body through a probe whose contacts are arranged so that the two stimuli currents are orthogonal to each other. The two high frequency signals hetrodyne within the human muscle to produce a single low frequency stimuli, useful for the production of muscle contraction, hyperemia, electroanalgesia and muscle relaxation.

6 Claims, 1 Drawing Figure

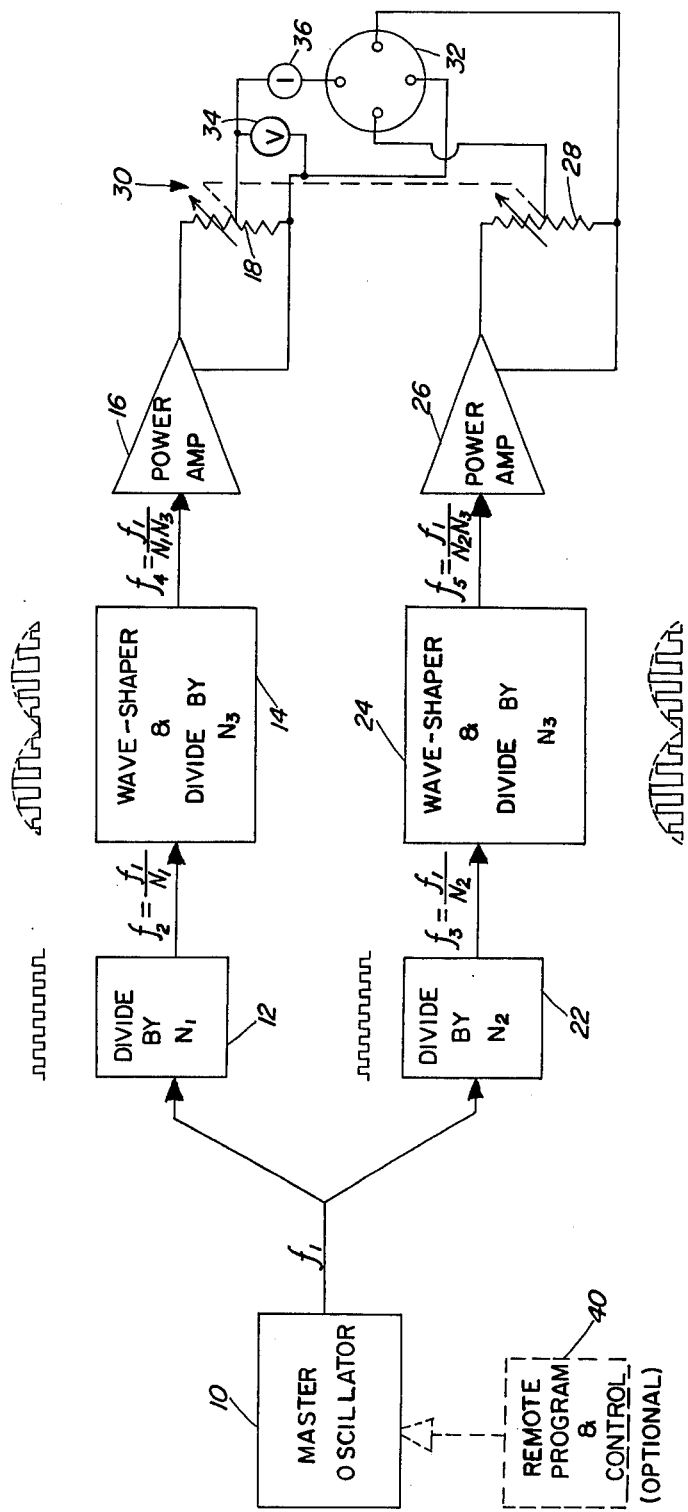

ELECTROTHERAPEUTIC DEVICE WITH MODULATED DUAL SIGNALS

BACKGROUND OF THE INVENTION

1. Field of the Invention

This invention relates to electrotherapeutic devices, and more particularly to apparatus for applying two separate frequencies of electrotherapeutic currents to the body of the patient each of said frequency currents being applied as a repeating series of pulses with a predetermined waveshape during a predetermined period.

2. Description of the Prior Art

From the earliest times of electrical knowledge, the response of organic tissue to the stimulus of electric current has been known. The first detailed scientific investigation of these effects was performed in Italy by Luigi Galvani, professor of anatomy at the University of Bologna. Due to the primitive state of development of electrical equipment in this era, his work was of necessity limited to application of steady-state DC and very low frequency (manually pulsed) AC. Galvani also observed and investigated the effects upon organic tissue of the induced energy resulting from the spark discharge of a nearby electrostatic generator, such discharges being largely oscillatory in nature and containing components of several frequencies.

Many studies were performed during the 19th century by many workers involving the application of electrical currents to the human body for medical purposes, with such studies devoted to the effects of various intensities, frequencies, directions of current flow, and electrode arrangement. Various apparatus for applying electrotherapeutic currents to the body of a patient have been developed. For example, U.S. Pat. No. 1,425,743 - Baruch which issued in 1922 covered an apparatus which produced an alternating electrostatic field of a plurality of different frequencies so that a hetrodyne effect was produced within the tissue of the patient. Similarly, French Pat. No. 859,618 published Dec. 23, 1940 describes an electrotherapeutic method which comprises the application to the body of two high frequency currents which intersect within the tissue of the patient so that upon intersection, a beat frequency equal to the difference between the two high frequencies resulted and was experienced by the patient. Similar heterodyne effect electrotherapeutic devices have been developed. For example, U.S. Pat. No. 2,622,601 - Nemec and U.S. Pat. No. 3,096,768 - Griffith disclose electrotherapeutic devices for producing and applying two separate signals of different frequencies to the body of the patient to produce heterodyne "beat" frequency sensation. Our own U.S. Pat. No. 3,794,022 discloses a dual oscillator, variable pulse duration electrotherapeutic device for producing series of square wave voltage pulses at two different frequencies, with the square wave pulses increasing in duration during repeating intervals, and the two frequencies intersecting within the body.

As is well known in the art, the stimulating effect of therapeutic electrical current is dependent on the form of the individual impulses and the frequency and intensity of the pulses. Furthermore, it is a well-known phenomenon of human physiology that a constant application of a sensoral stimuli to the nervous system has the effect of desensitizing the nerves over a period of time. Consequently, if the purpose of the electrotherapeutic device is to produce an anaesthesia of a particular portion of the body, a constant unvarying electrotherapeutic current should be applied to the area. However, where it is desired to limit the desensitization of the area to be treated, a constantly varying electrotherapeutic impulse should be applied to the area to be treated such as described in applicants' U.S. Pat. No. 3,794,022, issued Feb. 26, 1974.

Further, to provide maximum therapeutic reults, it is often desirable to apply various frequencies of electrotherapeutic current to the body of the patient. However, rather than utilizing the heterodyne effect between two frequencies to create a low frequency sensation to the patient, essentially the same sensation may be created by applying pulsed currents of a very low frequency.

SUMMARY OF THE INVENTION

An electrotherapeutic device for applying therapeutic electrical currents to the body of a patient comprises a single basic frequency source operating at a predetermined first frequency from which two separate frequency stimuli of constant frequency difference are derived using two frequency dividers to divide the first frequency by separate numbers. The two high frequency stimuli heterodyne within the human muscle to produce a single low frequency stimuli, useful for the production of muscle contraction, hyperemia, electro-analgesia and muscle relaxation. The output of each of the two frequency dividers is connected respectively to a separate waveshaper which similarly shape the two signals to any desired shape for the desired therapeutic effect. There are two power amplifiers connected respectively to the outputs of the waveshapers, with voltage amplitude control. A probe is provided to apply the outputs of the two power amplifiers to the body of the patient, so that the stimuli intersect within the muscle.

Preferably, the waveshapers also each include frequency dividers for dividing the frequencies of the two signals by the same number. The voltage control may be provided by two variable resisters (potentiometers) connected respectively to the outputs of the power amplifiers.

If it is an object of this invention to provide stable electrotherapeutic device, with two signals whose frequency is a predetermined constant difference.

Another object of the invention is to provide an electrotherapeutic device whose stimulus envelope may be altered to any predesigned shape, which can be square, ramp, exponential, sine, semi-sine, and biphasic or monophasic.

A further feature of the invention provides means so that the stimuli can be externally or internally programmed to any sequency of operation desired.

These and other objects, advantages, and features shall hereinafter appear, and for the purposes of illustration, but not for limitation, an exempliary embodiment of the present invention is illustrated in the accompanying drawings.

BRIEF DESCRIPTION OF THE DRAWING

The drawing is a functional block and schematic drawing of a preferred embodiment of the present invention.

DETAILED DESCRIPTION OF THE INVENTION

Referring to the block diagram in the drawing, the stimuli is initiated by a master oscillator 10 whose generated frequency output is designated f1. The output of this oscillator is split and applied simultaneously to the two divider stages 12 and 22 which divide the applied frequency by the factors N1 and N2 respectively. The output frequency of divider 12 is $f2 = f1/N1$ and the output frequency of divider 22 is $f3 = f1/N2$. Thus, two separate voltage stimuli are generated having a frequency difference of $f2 - f3$, where f2 is greater than $f3$.

The output of divider 12 is applied to wave shaper 14, while the output of divider 22 is applied to wave shaper 24. The wave shaper circuits serve to transform the constant amplitude pulse trains into amplitude modulated stimuli. In addition in the preferred embodiment the wave shaper circuits each also include further divider circuits to divide the pulse trains by a factor N3. Thus, the two stimuli frequencies become $f4 = f1/N1\,N3$, and $f5 = f1/N2\,N3$. Wave shapers 14 and 24 may be a variety of well known wave shaping circuits that could produce a semi-sinusoidal wave shape (as illustrated) as well as square, exponential, ramp, or any variation of these as desired.

The outputs of the wave shapers 14 and 24 are then applied to their respective power amplifiers 16 and 26, and then to the output control 30 which comprises a ganged dual potentiometer having adjustable resister sections 18 and 28 at the outputs of power amplifiers 16 and 26 respectively. The output control provides for the adjustment of the stimuli to any desired level in a continuously variable manner.

The adjusted stimuli are then applied to the human body through the interfacing applicator or probe 32 whose contacts are arranged in such a manner so that the two stimuli currents are orthogonal to each other. The adjusted output stimuli ar monitored by two indicators; a voltmeter 34 and an ammeter 36.

In a typical application, the frequency f1 of the oscillator may be 3.579545 MHz, the numbers N1 and N2 of the dividers 12 and 14 respectively may be 225 and 254, making the frequencies $f2$ and $f3$ respectively 14037.43 Hz and 14092.69 Hz, and the number N3 of wave shapers 14 and 24 may be 5, making the frequencies $f4$ and $f5$ respectively 2807.48 Hz and 2818.53 Hz. The output power measured by the meters 34 and 36 might be in the range of 50 volts and 100 milliamperes.

The drawing shows the output of waveshapers 14 and 24 modulated with a semi sine wave form. The time period between zeros may for example be 100 milliseconds. This form of waveshaping is useful to produce a therapeutic effect but other wave shapes may also be used.

Circuits for use in the various blocks of the drawing are readily available in the form of integrated circuit chips, or they may be assembled from discrete devices on printed circuit boards. The frequency dividers are typically comprised of counters using flip-flops or other bistable devices; which may be organized as binary counters or any other form of counting. The outputs of the flip-flops are decoded to obtain the value of N or N/2 in each divider, the decoder output being used to reset the counter and generate an output level change as by switching the state of another flip-flop.

Any of the known amplitude modulation techniques may be used in the wave shapers 14 and 24. The modulating signal could be common to the two wave shapers. The divide by N3 step may be accomplished either before or after the modulation operation.

The beat-frequency oscillation of the two stimuli is constant. Since $f4\,N1 = f1/N3$ and $f5\,N2 = f1/N3$; it follows that $f4/f5 = N2/N1$. The ratio between the dividers N2/N1 is a constant.

The remote program and control block 40 is optional. If provided it can be used to frequency modulation the beat frequency between $f4$ and $f5$. This is accomplished by shifting the master oscillator frequency $f1$.

Thus, it may be seen that a new and improved electrotherapeutic device for applying therapeutic electric currents to the body of a patient has been provided. This device provides additional advantages over the prior art electrotherapeutic devices since it applies two separate high frequency currents to the body of the patient with great stability and a precisely constant ratio between the frequencies so that the beat frequency is constant. The device provides stimuli which can be externally or internally programmed to any sequence of operation desired. The stimulus envelope may be shaped to any predetermined wave-shape which can be square, ramp, exponential, sine or any combination of them and be monophasic or biphasic in polarity. Note that the output meters 34 and 36 provide that the output magnitude is displayed to indicate the true r.m.s. voltage and current, irrespective of stimulus waveform.

It should be expressly understood that various changes, alterations and modifications may be made in the above described apparatus without departing from the spirit and scope of the present invention, the features of which are set forth in the accompanying claims.

We claim:

1. An electrotherapeutic device for applying thereapeutic electrical currents to the body of a patient comprising: oscillator means for producing first electric signals of a predetermined first frequency;

first and second divider means connected to receive said first electrical signals and to divide the frequency thereof by first and second numbers respectively to produce second and third signals respectively;

first and second waveshaping means connected respectively to receive said second and third signals and to shape the envelopes for these signals in a corresponding predetermined manner to produce respectively fourth and fifth signals;

first and second power amplifier means connected respectively to amplify said fourth and fifth signals; amplitude control means associated with said first and second power amplifier means to control the output voltage level of the outputs of said first and second power amplifier means;

applicator means for receiving said amplified fourth and fifth signals from the first and second power amplifier means respectively and applying these signals to the body of the patient.

2. An electrotherapeutic device as claimed in claim 1, wherein said first and second waveshaping means each include further divider means to divide the frequency of said second and third signals by the same third number in producing said fourth and fifth signals respectively.

3. An electrotherapeutic device as claimed in claim 1, wherein said amplitude control means comprises two variable resistors, connected respectively between the outputs of said power amplifier means and said application means, the resistors being ganged to a common mechanical control.

4. An electrotherapeutic device as claimed in claim 1, further including a remote program and control means coupled to control said oscillator means.

5. An electrotherapeutic device as claimed in claim 1, wherein said first and second wave shaping means provide modulation of said fourth and fifth signals in the form of monophasic semi-sine wave such a produced by a full wave rectifier from a full sinewave.

6. An electrotherapeutic device as claimed in claim 1, further including meter means to indicate the true root mean square value of the outputs to said probe means, with any stimulus waveform.

* * * * *